(12) United States Patent
Cox et al.

(10) Patent No.: US 8,586,362 B2
(45) Date of Patent: Nov. 19, 2013

(54) METHOD FOR DNA DOUBLE-STRAND BREAK REPAIR IN VITRO AND APPLICATIONS THEREOF

(75) Inventors: Michael M. Cox, Oregon, WI (US); John R. Battista, Baton Rouge, LA (US); Audrey J. Klingele, Madison, WI (US); Joseph R. Piechura, Hartford, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 559 days.

(21) Appl. No.: 12/796,258

(22) Filed: Jun. 8, 2010

(65) Prior Publication Data

US 2010/0317009 A1     Dec. 16, 2010

Related U.S. Application Data

(60) Provisional application No. 61/185,868, filed on Jun. 10, 2009, provisional application No. 61/268,255, filed on Jun. 10, 2009.

(51) Int. Cl.
*C12Q 1/68* (2006.01)
*C12N 15/00* (2006.01)

(52) U.S. Cl.
USPC .......................................... 435/440; 435/6.18

(58) Field of Classification Search
None
See application file for complete search history.

(56) References Cited

U.S. PATENT DOCUMENTS 6,333,178 B1    12/2001  Livneh et al.
2012/0082990 A1 *  4/2012  Piepenburg et al. ......... 435/6.12

FOREIGN PATENT DOCUMENTS

WO        WO03072805 A2      9/2003

OTHER PUBLICATIONS d'Abbadie M. et al., "Molecular breeding of polymerases for amplification of ancient DNA", Nat Biotechnol., 2007, 25 (8):939-943.
Blow N., "Exploring unseen communities", Nature, 2008, 453:687-690.
Butler J.M., et al., "Genetics and Genomics of Core Short Tandem Repeat Loci Used in Human Identity Testing", J Forensic Sci., 2006, 51(2):253-265.
Warnecke F., et al., "Building on basic metagenomics with complementary technologies", Genome Biol., 2007, 8 (12):231.
Xu L., et al., "A Dynamic RecA Filament Permits DNA Polymerase-catalyzed Extension of the Invading Strand in Recombination Intermediates", J Biol Chem., 2002, 277(16):14321-14328.
Burbano H.A., et al., "Targeted Investigation of the Neandertal Genome by Array-Based Sequence Capture", Science, 2010, 328(5979):723-725.
Cox M.M., et al. "Rising from the Ashes: DNA Repair in *Deinococcus radiodurans*", PLoS Genet., 2010, 6(1):e1000815.
PCT Notification of Transmittal, International Search Report, and Written Opinion, PCT/US2010/037793, Oct. 11, 2010.
Cox, Michael M., Recombinational DNA Repair in Bacteria and the RecA Protein, Progress in Nucleic Acid Research and Molecular Biology, 2000, vol. 63, pp. 311-366.
Kowalczykowski, Stephen C., Initiation of Genetic Recombination and Recombination-Dependent Replication, Trends in Biochemical Sciences, Apr. 2000, vol. 25, No. 4, pp. 156-165.
Pham, Phuong, et al., Roles of DNA Polymerases V and II in SOS-Induced Error-Prone and Error-Free Repair in *Escherichia coli*, Jul. 2001, PNAS, vol. 98, No. 15, pp. 8350-8354.

\* cited by examiner

*Primary Examiner* — Michele K Joike
(74) *Attorney, Agent, or Firm* — Quarles & Brady LLP

(57) ABSTRACT

A system and a method for DNA double-strand break repair in vitro are disclosed. Applications of the disclosed method in multiple areas are also disclosed.

7 Claims, 11 Drawing Sheets

DNA lengths

AatII – 2686bp, runs at an apparent 1.6kb when melted out as ssDNA

PstI – 2686bp

Self-ligated sticky ends (AatII-AatII product, not seen in gel) – 5372bp

Product 1 – approximately 3.2kb

Product 2 – approximately 4.8kb

Product/intermediate 3 – approximately 6.5kb

METHOD FOR DNA DOUBLE-STRAND BREAK REPAIR IN VITRO AND APPLICATIONS THEREOF

CROSS-REFERENCE TO RELATED APPLICATION

This application claims priority from U.S. provisional patent application Ser. No. 61/185,868 and U.S. provisional patent application Ser. No. 61/268,255, both of which were filed on Jun. 10, 2009 and are incorporated by reference herein.

STATEMENT REGARDING FEDERALLY SPONSORED RESEARCH OR DEVELOPMENT

This invention was made with United States government support awarded by the following agencies: US Department of Justice 2007-DN-BX-K146 and NIH GM067085 and GM032335. The United States government has certain rights in this invention.

BACKGROUND

In cells of all organisms, DNA double-strand breaks are repaired by a process involving the action of RecA-class recombinases, helicases, nucleases, DNA polymerases, and DNA ligases. A classical pathway for double-strand break repair, called synthesis-dependent single strand annealing (SDSA), is shown in FIG. 1. Briefly, nucleases and helicases are used to unwind the DNA at the broken end and degrade the 5'-ending strand. The region of single-stranded DNA (with a terminal 3' end) thus created is bound by a recombinase. The recombinase promotes a DNA strand invasion, to create a D-loop. The 3' end of the invading DNA strand can be extended by DNA polymerase. If the invading strand is then separated from the invaded DNA, it can be joined to its cognate broken end via strand annealing. Replication and DNA ligation completes the repair process.

Although SDSA may be the most common pathway for double strand break repair, other variants either exist or have been proposed. All variants share the key steps of rendering a DNA single stranded by the action of helicases and nucleases, DNA strand invasion promoted by a RecA-family recombinase, extension of the invading DNA 3' end with a DNA polymerase, and final ligation of nicks with DNA ligase.

What is needed in the art is a system for efficient repair of DNA double-strand breaks in vitro. Such a system will benefit multiple areas such as DNA genotyping in forensic science, DNA extraction from ancient sources, genome sequencing and metagenomics.

BRIEF SUMMARY OF THE INVENTION

The present invention relates generally to a method for joining two DNA fragments in vitro, both of which possess homologous DNA sequences, through a simplified process of DNA double-strand break repair. The method requires three proteins, RecA protein, the single-stranded DNA binding protein (SSB) and DNA polymerase I or homologues of these proteins.

In one embodiment, the present invention is a method of repairing a DNA double-strand break in vitro comprising the steps of: (a) providing a duplex DNA molecule wherein the molecule has a double-strand break and wherein the molecule is not super-coiled; (b) providing a single-stranded DNA (ssDNA) targeting fragment, wherein the targeting fragment is homologous to at least 15 nucleotides of the DNA molecule of step (a) (or providing a targeting fragment in a double-stranded form and converting the targeting fragment to single-strand DNA); (c) adding RecA protein or RecA protein homologue to the targeting fragment; (d) adding single-stranded DNA binding protein (SSB) or SSB homologue; (e) adding the DNA molecule of step (a) to the mixture resulting from step (d) and incubating until a strand invasion of the targeting fragment into the DNA molecule of step (a) has occurred; and (f) adding DNA polymerase and dNTPs, and incubating until an extended DNA comprising sequences from the targeting fragment and the DNA molecule of step (a) has been produced such that purification of the lengthened DNA is possible.

Preferably, step (c) is in the presence of a suitable buffer containing an ATP regenerating system. Preferably, the RecA protein and/or RecA homologue, SSB and/or SSB homologue, and DNA polymerase are from bacterial sources. More preferably, the RecA protein and/or RecA homologue, SSB and/or SSB homologue, and DNA polymerase are isolated from *Escherichia coli*.

In a preferred embodiment of the invention, the DNA polymerase is selected from the group consisting of DNA polymerase I, DNA polymerase V, phi29 DNA polymerase and engineered translesion synthesis DNA polymerases. Most preferably, the DNA polymerase is DNA polymerase I.

In another embodiment, the present invention is a kit for DNA double-strand break repair in vitro comprising an effective amount of (a) RecA protein or RecA protein homologue, (b) SSB or SSB homologue and (c) DNA polymerase. Preferably, the kit additionally comprises a suitable buffer for RecA protein or RecA homologue, containing an ATP regenerating system.

In another embodiment, the present invention is a method of repairing DNA double-strand breaks for forensic DNA genotyping comprising the steps of: (a) preparing at least a pair of single-stranded DNA fragments, wherein 3' end of each single-stranded DNA of a pair is proximal to an analyzed target region, with one single-stranded DNA fragment encompass homology to one side of the analyzed target region and the other single-stranded DNA fragment encompass homology to the opposite side of the analyzed target region; (b) adding RecA protein or RecA protein homologue to the single-stranded DNA; (c) adding SSB or SSB homologue; (d) adding a forensic, non-supercoiled DNA sample with a double-strand break and incubating until a strand invasion of the targeting fragments into the forensic DNA molecule has occurred; (e) adding DNA polymerase and dNTPs, and incubating until the invading DNA has been extended so as to comprise sequences from the targeting fragment and the forensic DNA molecule and until amplification or purification of the lengthened DNA is possible; and (f) analyzing the product of the reaction as part of a forensic DNA genotyping procedure. Preferably, the single-stranded DNA fragments encompass 15-2000 bp homology to regions flanking the analyzed target region. Even more preferably, the single-stranded DNA fragments encompass 150-400 by homology to regions flanking the analyzed target region. Most preferably, the single-stranded DNA fragments encompass 200-400 bp homology to regions flanking the analyzed target region.

In one embodiment of the invention, the single-stranded DNA of step (a) is directly synthesized by standard oligonucleotide synthesis methods that are widely and commercially available. In another embodiment, the single-stranded DNA of step (a) is converted from double-stranded targeting fragments. Preferably, the conversion of double-stranded targeting fragments to single-stranded DNA is via heat denaturation, asymmetric PCR, or specific degradation of the complementary strand by nucleases using a procedure that blocks the degradation of the desired strand or the combined activity of a nuclease/helicase combination. Preferably, step (b) is in the presence of a suitable buffer containing an ATP regenerating system.

In a preferred version of this embodiment, the target region is autosomal STR selected from the group consisting of D3S1358, D5S818, D7S820, D8S1179, D13S317, D16S539, D18S51, D21S11, CSF1PO, FGA, Th01, TPOX, and VWA.

In another version of this embodiment, the target region is Y chromosome STR. In yet another embodiment, the target region is mitochondrial DNA, which, when sequenced, can be used to identify an individual. Preferably, the target region of mitochondrial DNA is selected from the group consisting of hypervariable region 1 and hypervariable region 2 (nucleotides 16024-16576).

In a preferred version of this embodiment, the RecA protein and/or RecA homologue, SSB and/or SSB homologue, and DNA polymerase are from bacterial sources. More preferably, the RecA protein and/or RecA homologue, SSB and/or SSB homologue, and DNA polymerase are from *Escherichia coli*.

In a preferred embodiment of the invention, the DNA polymerase is selected from the group consisting of DNA polymerase I, DNA polymerase V, φ29 DNA polymerase and engineered translesion synthesis DNA polymerases. More preferably, the DNA polymerase is bacterial DNA polymerase I.

In another embodiment, the present invention is a kit for repairing DNA for forensic DNA genotyping, comprising: (a) at least two targeting DNA fragments that encompass the two DNA sequences immediately flanking a Short Tandem Repeat (STR) used for forensic DNA genotyping; (b) RecA protein or RecA protein homologue; (c) SSB or SSB homologue; and (d) DNA polymerase. Preferably, the kit additionally comprises a buffering solution that contains ATP and an ATP regenerating system, dATP, dGTP, dCTP and dTTP. Preferably, the kit comprises targeting DNA segments that flank an STR selected from the group consisting of the human genomic loci D3S1358, D5S818, D7S820, D8S1179, D13S317, D16S539, D18S51, D21S11, CSF1PO, FGA, Th01, TPOX, and VWA. Preferably, the targeting DNA fragment is designed such that the 3' end of the fragment corresponds to a position 2-10 bp away from the end of the STR, and STR sequences are not part of the targeting DNA fragments.

BRIEF DESCRIPTION OF DRAWINGS

The invention will be better understood and features, aspects and advantages other than those set forth above will become apparent when consideration is given to the following detailed description thereof. Such detailed description makes reference to the following drawings, wherein.

Figure 1:
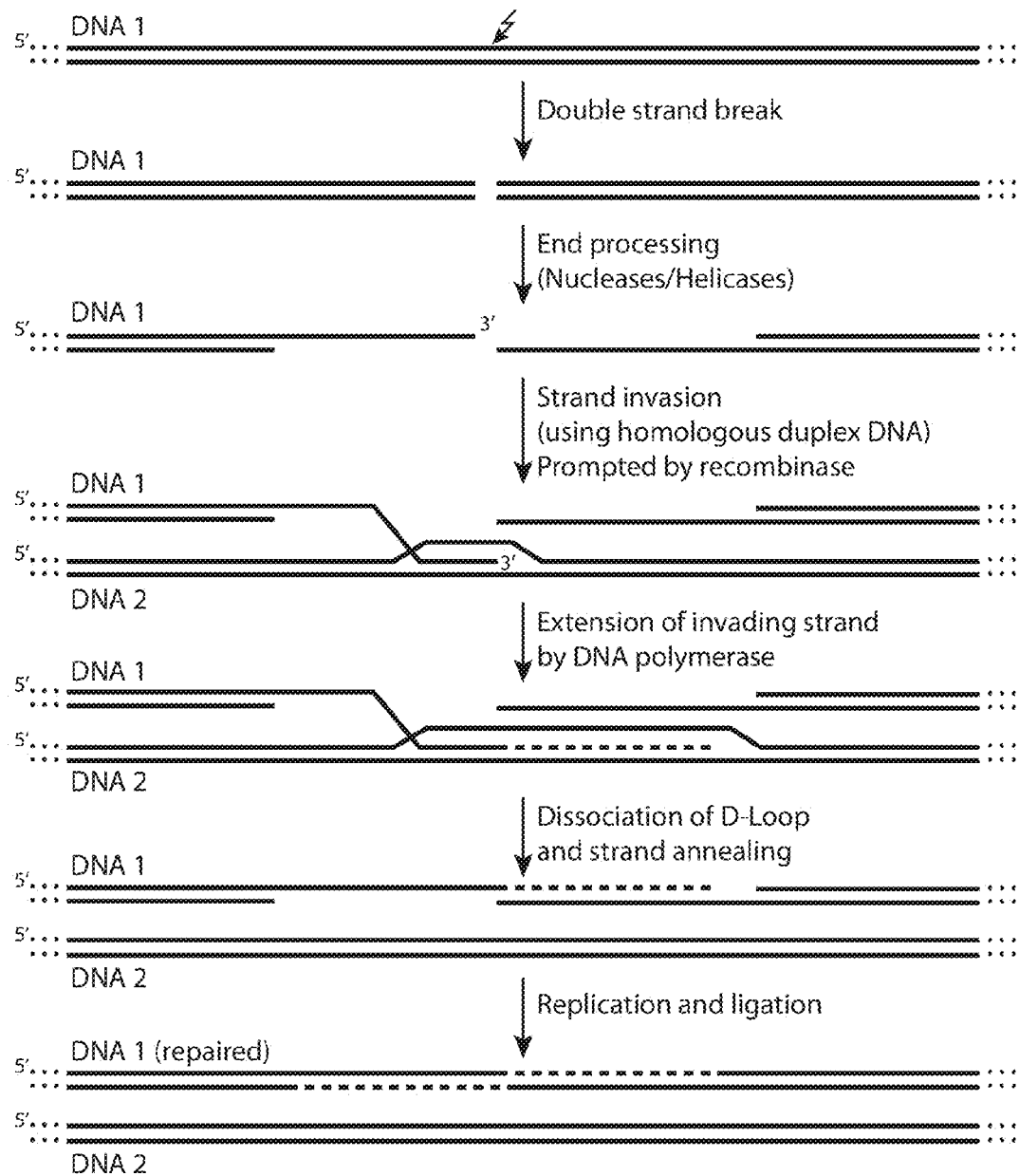
FIG. 1 shows a model for DNA double-strand break repair in vivo. The model shown is called synthesis-dependent strand annealing (SDSA) and exhibits many of the features of double-strand break repair in living cells. Once a double-strand break occurs (for example, due to effects of ionizing radiation), the broken DNA ends are processed by specific degradation of the 5'-ending strands. The exposed 3'-ending single-strands are bound by recombinases and used to invade a second intact homologous duplex DNA (DNA2 in the model). The invading end is extended by DNA polymerase (dashed line). The invading DNA dissociates from the intact duplex, and the now-lengthened DNA anneals with the exposed single-stranded DNA derived from the other broken end. Finally, remaining gaps are filled in by DNA polymerase and DNA ligase.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

BRIEF DESCRIPTION OF THE INVENTION

In General

We have developed a procedure for the joining together of two DNA molecules that share a significant region of homology, using a simple but robust in vitro double-strand break repair reaction. The process requires only three proteins: RecA protein, SSB and a DNA polymerase. Preferably, all three proteins are obtained from bacterial sources. More preferably, all three proteins are obtained from *Escherichia coli*.

The capacity to selectively target DNA sequences within a complex mixture is one of the most useful features of the method described herein. This method allows one to retrieve the proverbial "needle from the haystack" because the method relies on a RecA-facilitated search for complementarity between a targeting DNA fragment and the genomic DNA sequence with a double-strand break of interest. The mechanism of a RecA-mediated search for homology is not well understood, but in vitro evidence indicates that RecA can identify its target within an excess of 200,000-fold heterologous substrate within 15 minutes—far faster than if the same DNA fragment were added to this mixture in the absence of RecA (Bazemore, L. R., et al. 1997; Rao, B. J., et al. 1994).

Figure 2:
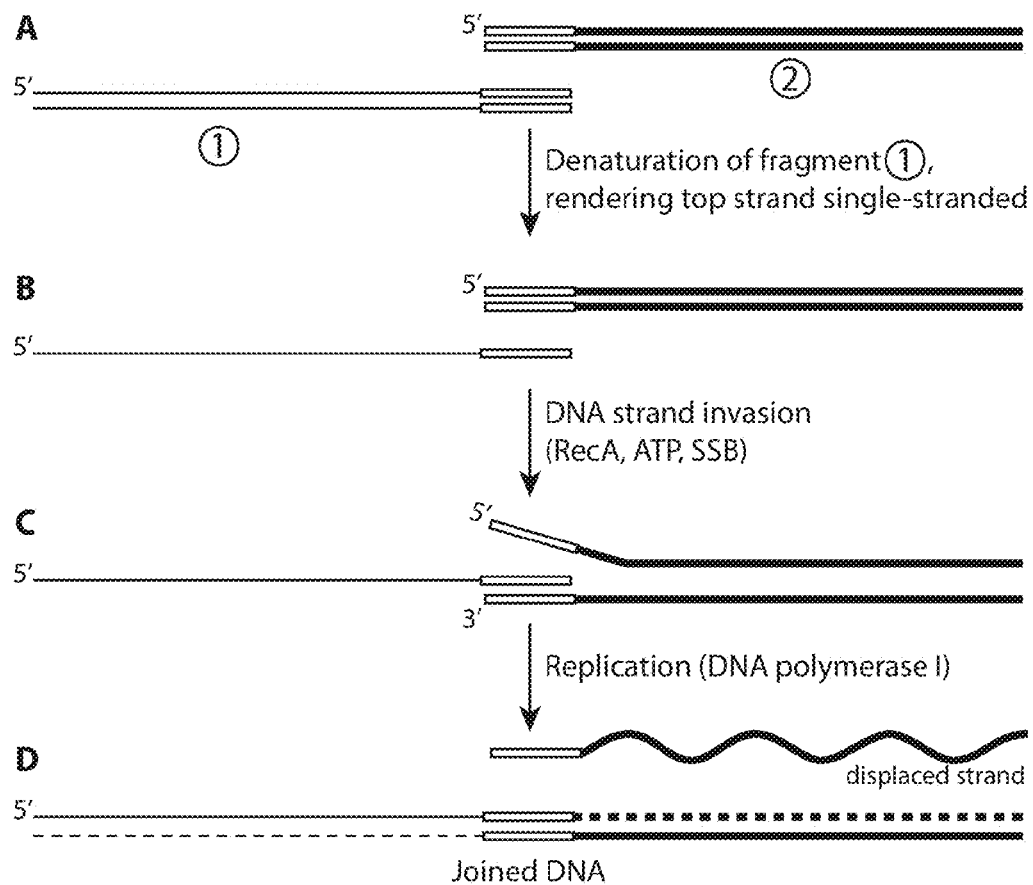
FIG. 2 is an embodiment of the present invention and shows a double-strand break repair reaction in vitro. The reaction shown is the splicing together of two DNA segments with an overlapping region of sequence, shown as open bar. One of the segments is rendered single-stranded, preferably by heat denaturation, nuclease/helicase action, or asymmetric PCR (PCR amplification using only one PCR primer). The 3'-ending strand is bound by RecA and SSB, and is used to invade the other duplex DNA. DNA polymerase I extends both available 3' ends and displaces one strand of DNA segment 2. The result is a new segment in which the sequences of segments 1 and 2 are combined.

FIG. 2 illustrates the mechanism of the method described herein. Referring to FIG. 2, fragment 2 represents a duplex genomic sequence of interest that has suffered a double-stranded DNA break. Fragment 1 represents a DNA fragment that will target a homologous region and allow fragment 2 to be lengthened and "repaired". The DNA shown in open bar represents DNA sequences shared by the two fragments. The targeting fragment is rendered single-stranded, such that the 3' ending strand (at the end with the common [open bar] DNA sequences) is preserved.

By "targeting fragment" we mean a segment of DNA designed to share homology, typically of at least 15 nucleotides, preferably of at least 18 nucleotides, with a genomic duplex DNA sequence of interest. Preferably, homology is 15-500 nucleotides, even more preferably 18-500 nucleotides, most preferably 20-50 nucleotides. The targeting DNA fragment may be initially double-stranded and rendered single-stranded via a variety of techniques, most preferably (a) heat denaturation, (b) asymmetric PCR, or (c) specific degradation of the complementary strand by nucleases using a procedure that blocks the degradation of the desired strand, or by the combined activity of a nuclease/helicase combination (FIG. 2B). Alternatively, the targeting fragment may be directly synthesized as a single-stranded molecule.

The single-stranded DNA targeting fragment is then bound by RecA protein or a RecA homologue and SSB or an SSB homologue in a suitable buffer containing an ATP regenerating system, and used to promote a strand invasion reaction into the duplex genomic DNA sequence with a double-strand break. (FIG. 2C). One would understand that, only when strand invasion has occurred successfully, DNA products can be amplified by polymerase chain reaction (PCR) and detected later on. A preferable buffer has a pH of 6.0 to 8.5, most preferably a pH of 6.5 to 8.5, and magnesium ion concentration of 1-15 mM, most preferably 1-10 mM. Recipes for preferable buffers are described, for example, in Shan, Q., et al., 1996, Cox, J. M., et al., 2008 and Gruenig, M. C., et al., 2008.

The 3' end of the invading targeting strand is then extended by DNA polymerase, preferably DNA polymerase I, displacing one strand of the invaded duplex DNA in the process (FIG. 2D). The 3' end of the invaded duplex is also extended by DNA polymerase I (FIG. 2D). The result is a lengthened DNA that combines sequences from both DNA fragments.

It is a feature of the present invention that the genomic DNA sequence of interest is not in a super-coiled state. Virtually all of the in vitro demonstrations of RecA-mediated strand invasion to date have made use of supercoiled target DNA. Supercoiled DNA is DNA that has been underwound relative to normal B-form DNA. In other words, it has fewer helical turns than the most stable form of DNA, and is thus in a strained state. In that state, it is easier to separate its two strands over short distances, a factor that helps to stabilize the products of strand invasion. To be in the strained supercoiled state, the DNA must be in a circular, unbroken form, or the supercoiled state must be maintained by bound proteins such as eukaryotic histones. Forensic DNA samples or ancient DNA samples or DNA isolated from bacterial populations is virtually never supercoiled, since it contains strand breaks. Even one strand break in a circular DNA will eliminate any supercoiling that exists. Hence, in the present invention, the capacity to use DNA that is not supercoiled is essential. Any linear fragment of DNA that is collected at a crime scene or in an ancient bone fragment has ends and is not supercoiled. The DNAs in the figures are drawn as linear fragments for just this reason.

To exploit the specificity of this reaction, the targeting DNA fragment may include at its 5' end a feature that allows efficient retrieval of that fragment and any DNA with which it has recombined. Non-limiting examples of this feature include a ligand such as biotin that can be harvested with streptavidin-coated magnetic beads, or a DNA sequence that binds tightly to a specific protein affinity column. Retrieving the targeting fragment and the target in this manner allows concentration of the target sequence and further manipulation of the target (eg PCR amplification) without the potential interference of biological and chemical contaminants found in the mixture from which the target was obtained.

Homologues and variants of RecA protein, SSB and/or DNA polymerase I can be used as substitutes. By "homologues and variants", we mean that minor or conservative amino acid substitutions may be introduced to the protein and still result in a protein with equivalent functional activity.

Specifically, we mean to define functional activity of DNA polymerase in terms of adding free nucleotides to the 3' end of a pre-existing DNA strand. For example, DNA polymerase V, φ29 DNA polymerase (Blanco, L., et al., 1984) and engineered translesion synthesis DNA polymerases (d'Abbadie, M., et al., 2007) can substitute for DNA polymerase I in the system described above. Other DNA polymerases may also be effective.

By homologue or variant of RecA, we mean to include proteins with similar structure and functional activity and at least 20% sequence identity to the bacterial RecA protein at the amino acid level. We mean to define the functional activity of RecA as searching for complementarity between a targeting DNA fragment and the genomic DNA sequence with a double-strand break of interest as well as the subsequent DNA binding and DNA invasion. We envision that RecA mutants that are more effective than the wild type RecA protein can be created and substitute the RecA protein in the method described herein. For example, we know that the reaction is enhanced by the RecA protein mutant called E38K. Other recombinases that can substitute are (a) RecA proteins from other bacterial species (all such recombinases from bacteria are called RecA; recombinases in the same family, but from different classes of organisms, have some different names, as follows), (b) RecA family recombinases from bacteriophages, such as the UvsX protein of bacteriophage T4, (c) the eukaryotic Rad51 and Dmc1 proteins, and (d) the RadA proteins of archaeans. We know that the *E. coli* RecA works well, and the RecA proteins from *Deinococcus radiodurans* and *Pseudomonas aeruginosa* also work in our trials (*Deinococcus* not as well as *E. coli*, and *Pseudomonas* RecA about as well as *E. coli* RecA).

By homologue or variant of SSB, we mean to include proteins from all organisms that are homologous to SSB and have the same function. We mean to define the function of SSB as binding single-stranded regions of DNA to prevent premature annealing and to enhance the DNA binding and DNA strand invasion activities of RecA protein. All the bacterial species have such proteins, and most are called SSB. An exception is an unusual type of SSB in *Deincoccus radiodurans*, which is called DdrB. The comparable protein in eukaryotes is called Replication Protein A (RPA), and the comparable proteins in archaeans are called SSB. We envision that any of these proteins may substitute for SSB in the method described herein. We have tried the SSBs from *E. coli, Deinococcus radiodurans*, and *Pseudomonas aeruginosa* so far, and all work.

One may evaluate equivalent functional activity of RecA, SSB and DNA polymerase I by reference to the Examples and the DNA double-strand break repair system disclosed below.

Preferably, one would obtain RecA protein, SSB and DNA polymerase I from the following sources: *E. coli, Deinococcus radiodurans, Thermus aquaticus, Pseudomonas aeruginosa, Neisseria gonorrhoeae,* and *Acinetobacter baylii.*

Forensic Applications

The method described above can be used to repair double-strand breaks in forensic DNA samples and, thus, restore DNA evidence samples that are quantitatively and qualitatively inadequate for PCR-based genotyping to a usable condition. The process is designed to: (a) permit accurate amplification of STR loci in degraded DNA samples (See Example 3 for detailed information about STR); (b) prevent alteration of STR repeat length in the DNA sample to be analyzed; (c) prevent any additional degradation of or damages to the DNA sample to be analyzed. Notably, the method described herein does not involve the use of nucleases (with the exception of nuclease activities associated with DNA polymerase I), DNA ligases, DNA helicases, or DNA topoisomerases that could alter STR properties critical to STR analysis. A preferred prophetic forensic method is described below.

Therefore, the present invention is a method of repairing DNA double-strand breaks for forensic DNA genotyping typically comprising the steps of: (a) providing at least two double-stranded targeting fragments, wherein the targeting fragments encompass 200-400 bp of homology on both regions flanking an analyzed STR, and converting the double-stranded targeting fragments to ssDNA, or simply synthesizing the targeting fragment as a single-stranded DNA; (b) adding RecA protein or RecA protein homologue to the ssDNA; (c) adding SSB or SSB homologue; (d) adding a forensic, non-supercoiled DNA sample with a double-strand break and incubating until a strand invasion of the targeting fragments into the forensic DNA molecule has occurred; (e) adding DNA polymerase and dNTPs, and incubating until the invading DNA has been extended so as to comprise sequences from the targeting fragment and the forensic DNA molecule and until amplification or purification of the lengthened DNA is possible; and (f) analyzing the product of the reaction as part of a forensic DNA genotyping procedure. The repaired forensic DNA can be isolated as soon as the sample contains repaired DNA segments encompassing the entire region surrounding a targeted STR that is typically amplified by RCR in standard forensic DNA genotyping procedures. By "analyzing the product of the reaction", we mean the standard PCR amplification of a DNA segment encompassing a targeted STR, followed by resolution of the amplified DNA segments by gel electrophoresis and the determination of their size, as outlined for forensic genotyping procedures in FIG. 4.

By "flanking", we mean preferably that the targeting DNA fragment should be homologous to the DNA region to one side of the STR and have its 3' end within 0-10 bp to one side of the STR. Preferably, step (c) is in the presence of a suitable buffer containing an ATP regenerating system. A preferable buffer has a pH of 6.0 to 8.5, most preferably a pH of 6.5 to 8.5, and magnesium ion concentration of 1-15 mM, most preferably 1-10 mM. Recipes for preferable buffers are described, for example, in Shan, Q., et al., 1996, Cox, J. M., et al., 2008 and Gruenig, M. C., et al., 2008. Preferably, the conversion of targeting fragments to ssDNA is via heat denaturation, asymmetric PCR, or specific degradation of the complementary strand by nucleases using a procedure that blocks the degradation of the desired strand or the combined activity of a nuclease/helicase combination. Alternatively, the targeting single-strand DNA fragments may be directly synthesized.

The materials needed for double-strand break repair of a forensic DNA sample are:

1. Purified Proteins

RecA protein or homologue (preferably from *E. coli*, although other RecA family recombinases may substitute)

Single strand DNA binding protein (SSB) or homologue (also preferably from *E. coli*, although SSB proteins from other species may substitute)

DNA polymerase I or homologue (preferably from *E. coli*, although other DNA polymerases may substitute, particularly translesion DNA polymerases such as DNA polymerase V of *E. coli*.)

2. A set of targeting single-stranded DNA fragments targeted to the STR sequences to be analyzed, with the targeting single-stranded DNA fragments being in pairs and each pair targeted to either side of one STR sequence to be analyzed. If 16 STR sequences are to be analyzed, then there will be 32 targeting DNA fragments. Each targeting fragment will typically be between 150-2000 base pairs in length, preferably 200-2000 base pairs in length. The 3' end of each targeting fragment will be identical to the sequence of the DNA flanking and on one side of the STR, from a point beginning a few base pairs from one end of the STR to a point beyond the sequence to which PCR primers are targeted to amplify the STR sequence in a modern forensic DNA genotyping protocol. For examples of typical forensic DNA genotyping protocols, see John Butler, 2006, Forensic DNA Typing.

Figure 7:
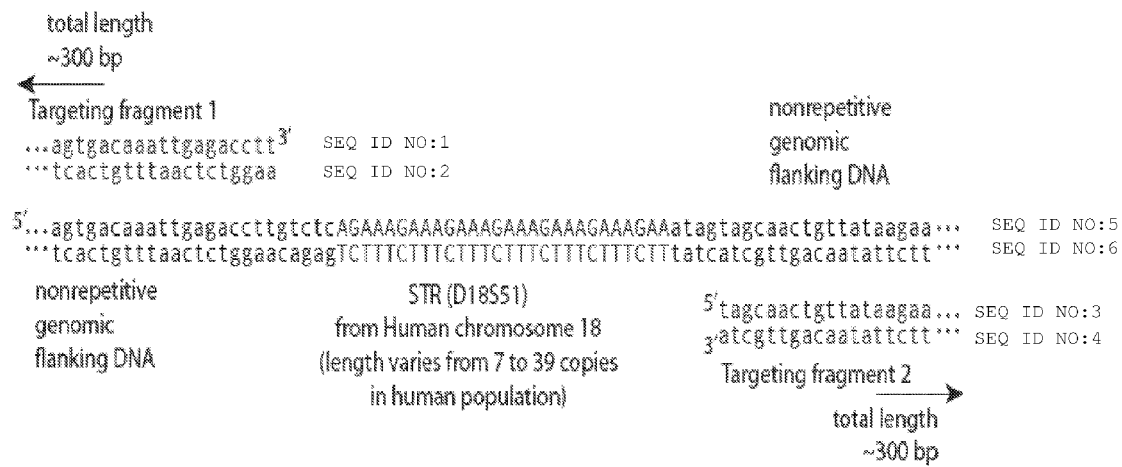
FIG. 7 shows the application of DNA double-strand break repair in vitro to forensic DNA typing near the STR labeled D18S51 (boxed), one of 13 STRs mandated to be included in forensic analyses as part of Combined DNA Index System (CODIS). D18S51 is found on human chromosome 18. Some of the nonrepetitive surrounding sequence is also shown (sequences in lower case letters). In this example, targeting fragments (shaded) will be designed as shown, including sequences that approach but do not encompass the STR itself. The targeting fragments must be long enough to encompass the sites homologous to the PCR primers used in typical DNA typing kits, and will generally be at least several hundred base pairs in length. The targeting fragment encompassing the nonrepetitive DNA to the left of the STR will be used to repair double strand breaks occurring in the region to the left of the STR. The other targeting fragment will be used to repair double strand breaks to the right of the STR. Two fragments are needed to repair conceivable breaks at each STR. Multiple sets of targeting fragments, 32 in total to cover the 16 loci targeted by a typical forensic DNA typing kit (the 13 CODIS loci plus three others that may differ from one kit to another), can be used together to target and repair double strand breaks near all of the STRs.

In FIG. 7, the targeting strands would be equivalent to the upper strand of fragment 1 (with sequences identical to the flanking DNA extending for several hundred additional nucleotides to the left), and the lower strand of fragment 2 (with sequences identical to the flanking DNA extending for several hundred nucleotides to the right). In every case, the targeting strand is identical to the flanking DNA strand that has its 3'-proximal end oriented towards the STR.

A useful reference to the STR sequences is the John Butler, 2006, *Forensic DNA Typing*. Note Table 1 for a list of most commonly used autosomal STR sequences. The 13 STRs listed in the claims and the examples are the thirteen specified by CODIS, and must be included in any forensic DNA typing kit used in the United States. Foreign law enforcement agencies use some of the same ones, but can have different ones specified as well. Current DNA typing kits use the 13 CODIS STR sequences, one locus called amelogenin (used to determine sex), and two other loci. By "current DNA typing kits", we mean those developed and marketed by Promega and Applied Biosystems, as well those developed and marketed by companies based in the European common market. The DNA typing kits are continually under development, but in all cases they include the 13 CODIS loci and a few extra STR loci. The "extra" STR loci are different for the Promega and Applied Biosystem kits.

In addition to autosomal STRs, non-autosomal targets, such as Y chromosome STRs and mitochondrial DNA sequences, can also be useful in some situations as disclosed in details in Example 3.

The protocol for conducting Y chromosome STR analysis is identical to that used in analysis of autosomal STRs, except a different set of loci is amplified. Targeting fragments specific could be designed, as described in paragraph [0034] for autosomal STRs, and used to retrieve Y chromosome STRs as necessary.

Analysis of mtDNA is currently accomplished by sequencing the DNA from hypervariable regions 1 and 2 (HV1/HV2) of the displacement loop (nucleotides 16024-16576) (Budowle, B., et al. 1999). The nucleotide polymorphisms found by sequencing identify the individual. As with the STRs, the hypervariable regions are flanked by conserved sequences that would allow their retrieval from complex mixture following double strand break repair, extending the use of the invention to all markers commonly used in forensic analysis.

3. A suitable buffer (e.g., Tris buffer at a concentration of 10-50 mM).

4. ATP or dATP or a non-hybrolyzable ATP analogue such as ATPγS.

5. An ATP regenerating system (Phosphoenolpyruvate and pyruvate kinase, or creatine phosphate and creatine kinase; the same systems will regenerate dATP).

6. The four deoxynucleoside triphosphates dCTP, dTTP, dATP, and dGTP.

Reaction temperatures would typically be set in the range 30-37° C. However, the reaction temperatures would be higher if proteins from a thermophilic bacterium such as *Thermus aquaticus* are used. The set of targeting fragments would first be incubated briefly (1-10 min) with RecA protein. SSB and ATP would then be added, followed by a few additional minutes of incubation. All of these components would typically be present in the low (1-10) μM range, although lower or higher concentrations may be called for in particular circumstances. The forensic DNA sample would then be added. After about 5-10 min of additional incubation, the DNA polymerase and dNTPs would be added. The reaction would be continued for 10-60 min.

The sample would then, either after deproteinization (using either added proteases, extraction of the DNA with phenol and chloroform or treatment with detergents such as sodium dodecyl sulfate [SDS]) or without further processing, be subjected to standard forensic DNA typing protocols as referred to in paragraphs [0041] to [0047].

TABLE 1

Properties of the Loci Used for the CODIS Database

| Locus | Chromosome | Repeat motif | Repeat length (range)* | Number of alleles seen† |
|---|---|---|---|---|
| CSF1PO | 5 | TAGA | 5-16 | 20 |
| FGA | 4 | CTTT | 12.2-51.2 | 80 |
| TH01 | 11 | TCAT | 3-14 | 20 |
| TPDX | 2 | GAAT | 4-16 | 15 |
| VWA | 12 | [TCTG][TCTA] | 10-25 | 28 |
| D3S1358 | 3 | [TCTG][TCTA] | 8-21 | 24 |
| D5S818 | 5 | AGAT | 7-18 | 15 |
| D7S820 | 7 | GATA | 5-16 | 30 |
| D8S1179 | 8 | [TCTA][TCTG] | 7-20 | 17 |
| D13S317 | 13 | TATC | 5-16 | 17 |
| D16S539 | 16 | GATA | 5-16 | 19 |
| D18S51 | 18 | AGAA | 7-39.2 | 51 |
| D21S11 | 21 | [TCTA][TCTG] | 12-41.2 | 82 |
| Amelogenin | X, Y | Not applicable | | |

Source: Adapted from Butler, J.M. (2006) Forensic DNA Typing, 2nd edition, Academic Press, San Diego, page 96.
*Repeat lengths observed in the human population. Partial or imperfect repeats can be included in some alleles.
†Number of different alleles observed to date in the human population. Careful analysis of a locus in many individuals is a prerequisite to its use in forensic DNA typing.

Other Applications

The protocols for application of the invention to metagenomics, ancient DNA and genome sequencing will be identical. For each application, there is a need for isolated DNA and enough DNA sequence information (at least 15 base pairs) to direct the generation of a targeting DNA fragment. Methods for isolating the DNA will vary with the application. There is no universal protocol for isolating the DNA and it will vary with the source of the DNA, but one skilled in the art will know what is needed after reviewing the disclosure herein. The DNA sequence information needed for the targeting fragment will exist because of previous efforts to obtain that information.

It is envisioned that one embodiment of the present invention is a method for extraction of specific DNA segments of interest from an ancient source. The double-strand break repair system described herein is readily applied to the recovery of DNA segments from ancient tissue and bone samples. One would first extract the DNA. A number of methods for ancient DNA extraction have been published; these include precipitation (Hänni, C., et al., 1995; Kalmar, T., et al., 2000) with either ethanol or isopropanol, filtration of extracts using DNA-specific membranes (Leonard, J. A., et al., 2000) and binding DNA to silica (Hofreiter, M., et al., 2004) The method involving binding DNA to silica in suspension is at present the gentlest method for recovering bulk DNA from ancient sources such as bone that are difficult to prepare. This method is described here, but any protocol for isolating DNA from ancient materials may be used.

Typical extraction and repair:
1. Grind the ancient tissue under liquid nitrogen to obtain approximately 100-10,000 mg of powder, preferably approximately 500 mg of powder.
2. Add an extraction buffer consisting of EDTA and proteinase K to remove any proteins present.
3. Combine the extract in (2) with a binding buffer consisting of 5 M guanidinium thiocyanate, 25 mM NaCl and 50 mM Tris and a suspension of silica. All DNA in the sample binds to the silica.
4. The silica is then washed extensively; the silica is retrieved and dried.
5. The DNA is then eluted from the silica with TE buffer. At this point the sample DNA will contain the ancient DNA of interest and potentially modern DNA from eukaryotic and bacterial sources.
6. One would then apply the DNA repair protocol disclosed above. The targeting fragment will contain DNA homologous to the ancient source DNA.

Due to its reliance on regions of homology between probe and target DNA, the double-strand break repair system described herein is highly specific for rare ancient DNA fragments and in many cases relatively unaffected by DNA contamination derived from modern organisms.

It is also envisioned that one embodiment of the present invention is a method to fill in sequencing gaps in genome sequencing projects. As whole genome shotgun sequencing projects near completion, it frequently becomes difficult to "close the genome"—that is, to fill in any remaining gaps in the DNA sequence (Tettelin, H., et al., 1999). Substantial effort is often needed to clone these last remaining sections and verify that the genome sequence is finished. The invention can eliminate this problem. Genomic regions that are difficult to sequence can be retrieved and cloned by double-strand break repair. Since the genome sequence on either side of a gap will be known, targeting DNA fragments will be generated that will allow retrieval of adjacent sequence from isolated genomic DNA. Genomic DNA will be isolated from the organism of interest using any of the commercially available kits for DNA isolation and purification (eg Wizard® Genomic DNA Purification Kit from Promega).

It is also envisioned that the method described herein will benefit the study of metagenomics by allowing investigators to isolate and characterize specific DNA sequences within the complex mixtures of DNA obtained from environmental samples. In principle, any environment from which DNA can be isolated is a potential target for metagenomic analysis. The procedure involves bulk isolation of DNA from the sample followed by random sequencing and the assembly of short "reads" into larger sequences by overlap. The methods for isolating DNA are as varied as the environments from which the samples are obtained. Epicentre Biotechnologies sells a "Metagenomic DNA Isolation Kit for Water." Also, there are a number of published protocols describing isolation of DNA from environmental samples, for example, see Rondon, M. R., et al., 2000.

The protocol for double strand break repair in a metagenomics DNA sample, ancient DNA sample, or for use in filling gaps during genome sequencing will be similar to that described for the STR typing protocol. A preferable protocol will be as below.

Materials:
  a. Purified proteins
    RecA protein (from *E. coli*, although other RecA family recombinases may substitute)
    Single strand DNA binding protein, or SSB (also from *E. coli*, although SSB proteins from other species may substitute
    DNA polymerase I (from *E. coli*, although again other DNA polymerases may substitute, particularly trans-lesion DNA polymerases such as DNA polymerase V of *E. coli*.
  b. Isolated DNA in solution from the sample of interest.
  c. A targeting single-stranded DNA fragment, designed to interact with a sequence of interest. Each targeting fragment will typically be one hundred to two hundred base pairs long. The 3' end of each targeting fragment will be complementary to the sequence of interest. The 5' end of the targeting fragment will be biotinylated.
  d. A suitable buffer (e.g., Tris buffer at a concentration of 10-50 mM)
  e. ATP
  f. An ATP regenerating system (Phosphoenolpyruvate and pyruvate kinase, or creatine phosphate and creatine kinase)
  g. The four deoxynucleoside triphosphates dCTP, dTTP, dATP, and dGTP.

Protocol
  a. Reaction temperatures will be set in the range 30-37° C. However, the reaction temperatures would be higher if proteins from a thermophilic bacterium such as *Thermus aquaticus* are used.
  b. The targeting fragment is incubated briefly (1-5 min) with RecA protein.
  c. SSB and ATP would then be added, followed by a few additional minutes of incubation. All of these components would typically be present in the low (1-10) µM range, although lower or higher concentrations may be called for in particular circumstances.
  d. The DNA sample would then be added. After about 5-10 min of additional incubation, the DNA polymerase and dNTPs would be added.
  e. The reaction would be continued for 10-60 min.
  f. The reaction will be stopped by adding a detergent compatible with recovery of the biotinylated fragment using streptavidin coated magnetic beads.
  g. Universal linkers (short duplex DNA oligonucleotides with sequences complementary to primers utilized by common DNA sequencing platforms) will be added to the bound DNA.
  h. The targeting fragments and captured DNA will be eluted from the magnetic beads.
  i. Captured DNA will be sequenced using primers specific for the universal linker and the targeting fragment.

Kits

In another embodiment, the present invention is a kit for DNA double-strand break repair in vitro. Preferably, the kit comprises an effective amount of RecA protein or RecA protein homologue, SSB or SSB homologue and DNA polymerase. A preferable kit would contain enough reagent for multiple reactions. For a typical reaction with a total volume of 5-20 µL, preferable amounts would be 0.1-10 units of DNA polymerase I or homologue, 50-2,000 ng of RecA protein or RecA protein homologue and 2-100 ng of SSB or SSB homologue.

In another embodiment of the invention, the kit would provide reagents for DNA double-strand breaks for forensic DNA genotyping. This kit would contain the reagents described above and primers directed specifically for targeted STRs. In a preferred version of a kit of the present invention, one would target at least one STR selected from the group consisting of D3S1358, D5S818, D7S820, D8S1179, D13S317, D16S539, D18S51, D21S11, CSF1PO, FGA, Th01, TPOX, and VWA. This kit would comprise, preferably, at least two primers. A primer would be positioned on each side of the STR so that double-strand break repair can occur in either direction. In another version of a preferred kit, the kit would contain pairs of primers designed to amplify the 13 STRs specified by CODIS, plus additional STRs that are targeted by the commercial forensic genotyping kit (typically from Promega or Applied Biosystems) being utilized by a given laboratory.

The following Examples are, of course, offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

EXAMPLES

Example 1

A System For DNA Double-Strand Break Repair In Vitro

FIG. 2 illustrates the mechanism of the method described herein. The DNA shown in open bar represents DNA sequences shared by the two fragments. One of the two DNA fragments is rendered single-stranded, such that the 3' ending strand (at the end with the common (open bar) DNA sequences) is preserved. The single-stranded DNA may be obtained via heat denaturation, asymmetric PCR, specific degradation of the complementary strand by nucleases using a procedure that blocks the degradation of the desired strand, or by the combined activity of a nuclease/helicase combination (FIG. 2B). Alternatively, the targeting single-strand DNA fragments may be directly synthesized. The single-stranded DNA targeting fragment is bound by RecA protein and SSB, and used to promote a strand invasion reaction into the other duplex DNA (FIG. 2C). The 3' end of the invading strand is extended by DNA polymerase I, displacing one strand of the invaded duplex DNA in the process (FIG. 2D). The 3' end of the invaded duplex is also extended by DNA polymerase I (FIG. 2D). The result is a lengthened DNA that combines sequences from both DNA fragments.

Figure 3A:
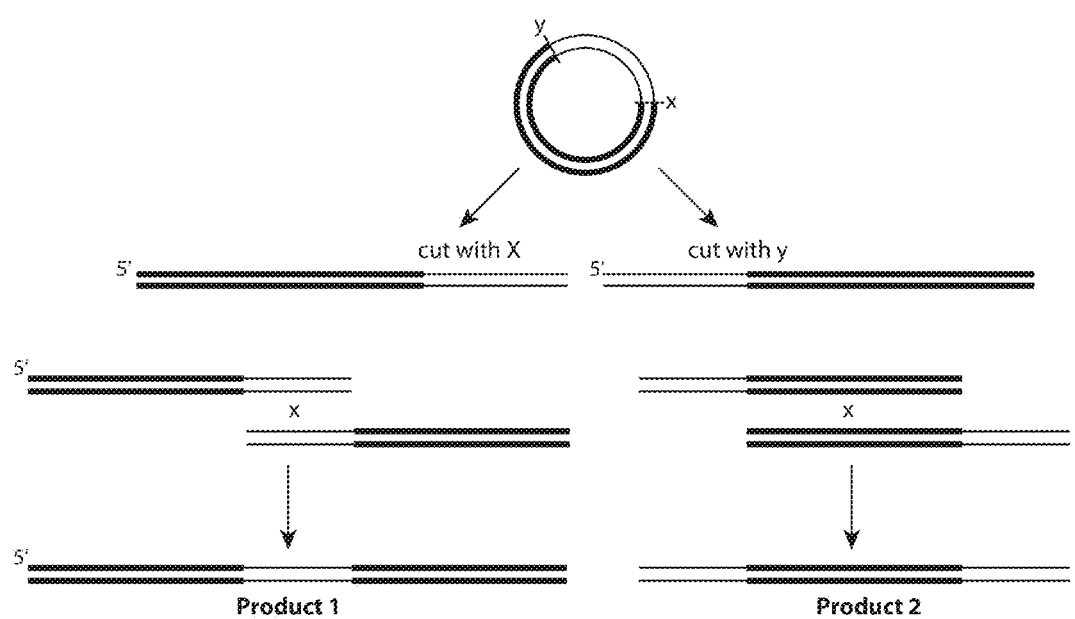
FIG. 3 A-C shows a test reaction designed to demonstrate the present invention. (A) A single plasmid DNA is cut in two different ways to generate two different full-length linear segments. These two segments have all the same nucleotide sequences, but the sequences at the ends are different, and the two segments can overlap in two different ways. This situation leads to two different double-strand break repair reactions and two possible products. (B) The plasmid used in this experiment is pUC19 (2686 bp), cleaved with either AatII or PstI. The first lane after the marker ladder shows heat-denatured AatII cleaved pUC19 (single-stranded DNA or ssDNA). Lane 2 shows PstI cleaved pUC19 (linear duplex DNA or dsDNA). Lane 3 shows both of these DNA substrates together. Lane 4 shows the ssDNA after 3 min of incubation with RecA protein (some has reannealed, some is in the well). Lane 5 shows the DNA after addition of RecA and SSB. Lane 6 shows the DNA after the addition of the dsDNA, just prior to the addition of DNA polymerase I. The final three lanes show the generation of products at 10, 20, and 30 min after the addition of DNA polymerase I. S: substrate DNA; P: expected products; I: reaction intermediates. (C) Requirements for double-strand break repair in vitro. The same marker ladder is used in lane 1, and lanes 2-4 are again simply the denatured and intact DNA segments, as in panel B. The next three lanes (5-7) show the effects of incubating the indicated components with denatured DNA (ssDNA) at 37° C. for 46 min. Lanes 8-10 show the same components incubated in the same way with intact dsDNA. Lanes 11-16 show reactions containing both DNA substrates. In lanes 11-15, one or more components were omitted. Lane 16 shows the complete reaction. Wherever DNA polymerase I was present, dNTPs were also added. Wherever RecA was present, ATP and an ATP regenerating system was also added. In the complete reactions shown, ssDNA and RecA were first mixed in a buffer containing ATP and an ATP regenerating system, and incubated at 37° C. for 3 min. SSB was then added, and the incubation continued for 3 min. The dsDNA was then added, followed by 10 min of incubation. DNA polymerase I and dNTPs were added last, with incubation continued for 30 min or as noted. When aliquots from a reaction were removed, the reactions were stopped by addition of proteinase K.
Figure 3B:
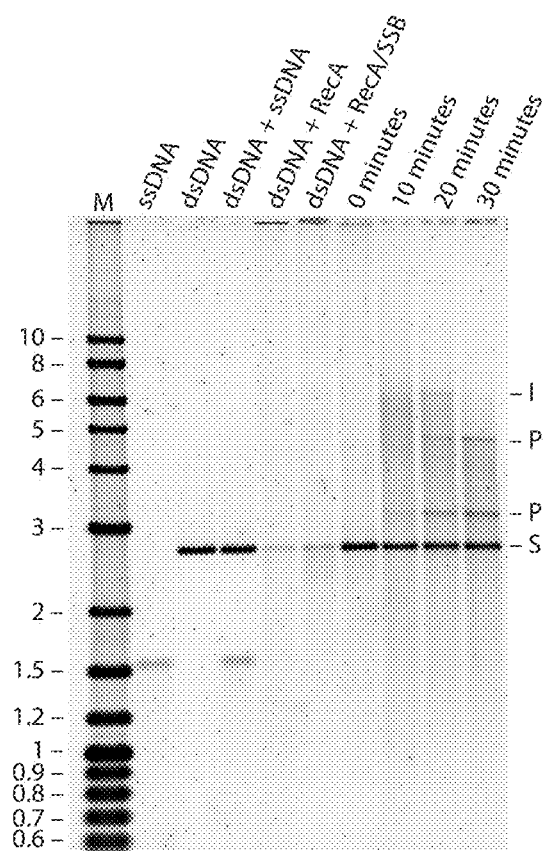
Figure 3C:
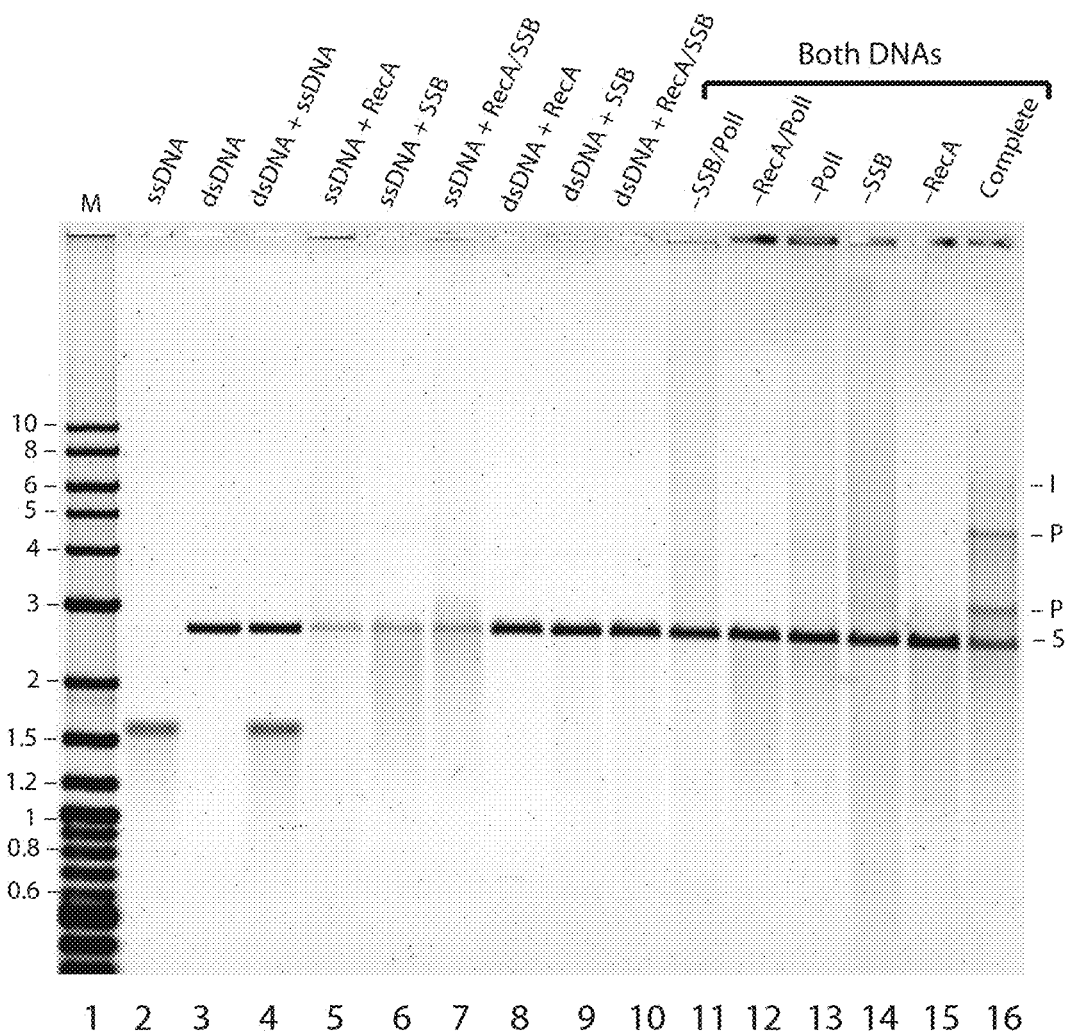

A specific test reaction is presented in FIG. 3. FIG. 3A is a scheme of the test reaction. In the test reaction, the two DNA fragments are derived from a single short plasmid. However, each fragment is derived by cleaving the plasmid in a different location. The fragments, thus, overlap in sequence at both of their ends, and two different invasion and replication reactions are possible. In one reaction, the shorter overlapping ends are involved, generating a long DNA product (product 1 in FIG. 3A). In the other reaction, the longer overlapping DNA ends are involved, generating a product that is not as long (product 2 in FIG. 3A). In FIG. 3B, a reaction time course is presented, showing the generation of both of the expected products. FIG. 3C demonstrates that the reaction is dependent on each of the three added proteins: RecA protein, SSB and DNA polymerase I.

Specifics of the double-stranded break repair test reaction are disclosed below:

Materials and Methods

Proteins, DNA, and Reagents

*Escherichia coli* proteins RecA and SSB were purified natively as described previously (Lohman et al., 1986; Shan et al., 1996).

DNA substrates were derived from pUC19 DNA that was purified using $CsCl_2$ banding. DNA was digested with either AatII or PstI (NEB (Ipswich, Mass.)). The reaction was then subjected to phenol/chloroform/isoamyl alcohol (25:25:1) extraction. Finally, the DNA was ethanol precipitated and resuspended in water.

DNA Polymerase I was purchased from NEB (Ipswich, Mass.). The dNTPs were purchased from Promega (Madison, Wis.). ATP, creatine phosphokinase, phosphocreatine, and DTT were purchased from Sigma (St. Louis, Mo.). SYBR Green I dye was purchased from Invitrogen (Carlsbad, Calif.).

Double-Strand Break Repair—The Reaction

The AatII digested pUC19 DNA was heated in water to 100° C. for 10 min in a thermocycler, then quick-chilled in an ice-water bath for 10 min. To this DNA (1.6 µM nucleotide (nt)) was added a reaction mix containing the following (concentrations reported as final): RecA buffer (25 mM Tris-Ac 80%+, 5% glycerol, 3 mM Potassium glutamate, 10 mM MgOAc), ATP (2 mM), DTT (1 mM), additional glycerol (7.5%), and an ATP-regeneration system of creatine phosphokinase (10 U) and phosphocreatine (12 mM). RecA protein (3 µM) was added and this reaction was incubated at 37° C. for 3 minutes. SSB protein (0.8 µM) was added and allowed to incubate at 37° C. for 3 minutes. The PstI digested pUC19 DNA was then added and allowed to incubate at 37° C. for 10 minutes. Finally, DNA Polymerase I (1 unit) was added with all four dNTPs (2 mM), and allowed to incubate at 37° C. for at least 30 minutes. Reactions were deproteinized with 1 µL of proteinase K (undiluted from manufacturer) and incubated at 37° C. for 30 minutes. Loading buffer (20 mM EDTA, 8.3% glycerol, 0.07% bromophenol blue, in water) was added to the reaction and the entire aliquot was loaded onto a 1% agarose/1×TAE gel for electrophoresis. Following electrophoresis, the gel was stained with SYBR Green I dye (Invitrogen (Carlsbad, Calif.)), and the DNA was visualized using an Amersham Typhoon imaging model 9410.

Relevant Results

The plasmid pUC19 DNA digested with AatII shares homology with the ends of the PstI digested pUC19 DNA. The ends overlap by 504 bp and 2182 bp. Strand-pairing, strand exchange, and extension of the 3' end of the exchanged strand can theoretically produce two products: one of 3190 bp and another of 4868 bp. So for example, invasion of the PstI digested pUC19 DNA with a single strand of AatII digested pUC19 DNA produces a joint molecule with two 3' ends that can be extended by DNA Pol I to produce a fully double-stranded molecule of the above mentioned lengths.

The results we obtained show the appearance of two products of almost equal intensity, of approximately 3.2 kb and 4.8 kb. The appearance of these two higher molecular weight bands is dependent on the presence of the two DNAs (AatII digested pUC19 that has been rendered single-stranded, and the PstI digested pUC19, which is double-stranded), RecA (in the presence of ATP), SSB, DNA PolI, and all four dNTPs. Omit any one of these components and the products are not formed. Thus, we have shown that these components (a ssDNA and a dsDNA sharing a region of homology, RecA (in the presence of ATP), SSB, DNA Polymerase I, and all four dNTPs) are both necessary and sufficient for product formation.

Linear regression of the product bands as compared to the molecular weight ladder correlates with the length of the hypothesized products within 10% (similar results were obtained for the starting substrates of known length). These results correlate with our theoretical results. Not seen in the gel are any bands of a length corresponding to two DNA fragments joined by simple ligation of their 3' overhangs (produced by restriction digest), which would be at 5372 bp. Additionally, though the efficiency of the reaction is not 100%, the observed intensity of the starting dsDNA substrate at 2686 bp can be seen to decrease as products of higher molecular weight appear, suggesting incorporation of starting substrate DNA into the final product. An additional band appearing at about 6.5 kb appears early in the reaction and then disappears, suggesting that it is an intermediate, possibly containing both double-stranded and single-stranded regions. Further supporting our hypothesis that this is an intermediate is that our theoretical experiment showing what length products could be produced does not support a product of this length (the closest hypothesized product lengths are 5876 bp and 7554 bp).

Example 2

The Use of Synthetic Oligonucleotides in the DNA Double-Strand Break Repair Reaction A specific single-strand DNA capture fragment can be chemically synthesized using available genome sequence data to guide the synthesis. The process is inexpensive and synthetic oligonucleotides as large as 200 nucleotides may be purchased commercially. The protocol for selective capture is simplified if biotinylated oligonucleotides specific for the target sequences of interest can be prepared on demand.

To test the feasibility of using synthetic oligonucleotides in the double strand break reaction, we designed biotinylated capture fragments of 50, 100, 150 and 200 nucleotides in length. Each fragment was complementary to DNA sequence upstream of the gltS gene of *Escherichia coli*, which simulated a target sequence. A double strand break reaction was conducted as described in paragraph [0076] of this application.

Materials and Methods

One nanomole of the biotinylated oligonucleotide was added to the reaction mixture composed of 1 mMDTT, 2 mM ATP, 7.5% glycerol, 12 mM phosphocreatine, and 10 U creatine phosphokinase. RecA from *E. coli* was then added to a final concentration of 2 µM, and incubated for three minutes at 37° C. SSB protein from *E. coli* was added to the reaction mixture to a final concentration of 0.8 µM, and incubated an additional three minutes at 37° C. 250 ng of target DNA was added to the reaction mixture and incubated for 30 minutes at 37° C. before the addition of one unit of DNA polymerase I from *E. coli* and deoxynucleotide triphosphates (2 mM final concentration). This final reaction mixture was incubated for 30 minutes at 37° C. The reaction was stopped by adding Proteinase K (1 mg/ml final concentration) for one half hour at 37° C., followed by the addition of phenylmethanesulfonyl fluoride (5 µM final concentration). Phenylmethanesulfonyl fluoride was left in the reaction mixture for one hour.

The streptavidin-coated magnetic beads (Dynal M-280) used to recover the capture fragment and bound target sequence from each reaction were washed twice in phosphate buffered saline prior to use. 50 µL of the washed bead suspension was combined with the reaction mixture and incubated for three hours at room temperature with agitation. The beads were separated from the reaction mixture with a magnet, and washed twice with phosphate buffered saline and once with deionized water. The magnet was removed; 95% formamide in 10 mM EDTA was added to the beads and the mixture was heated for 5 minutes at 65° C. A magnet was used to separate the free beads; the supernatant was collected to retrieve the captured target DNA.

Relevant Results

Figure 8:
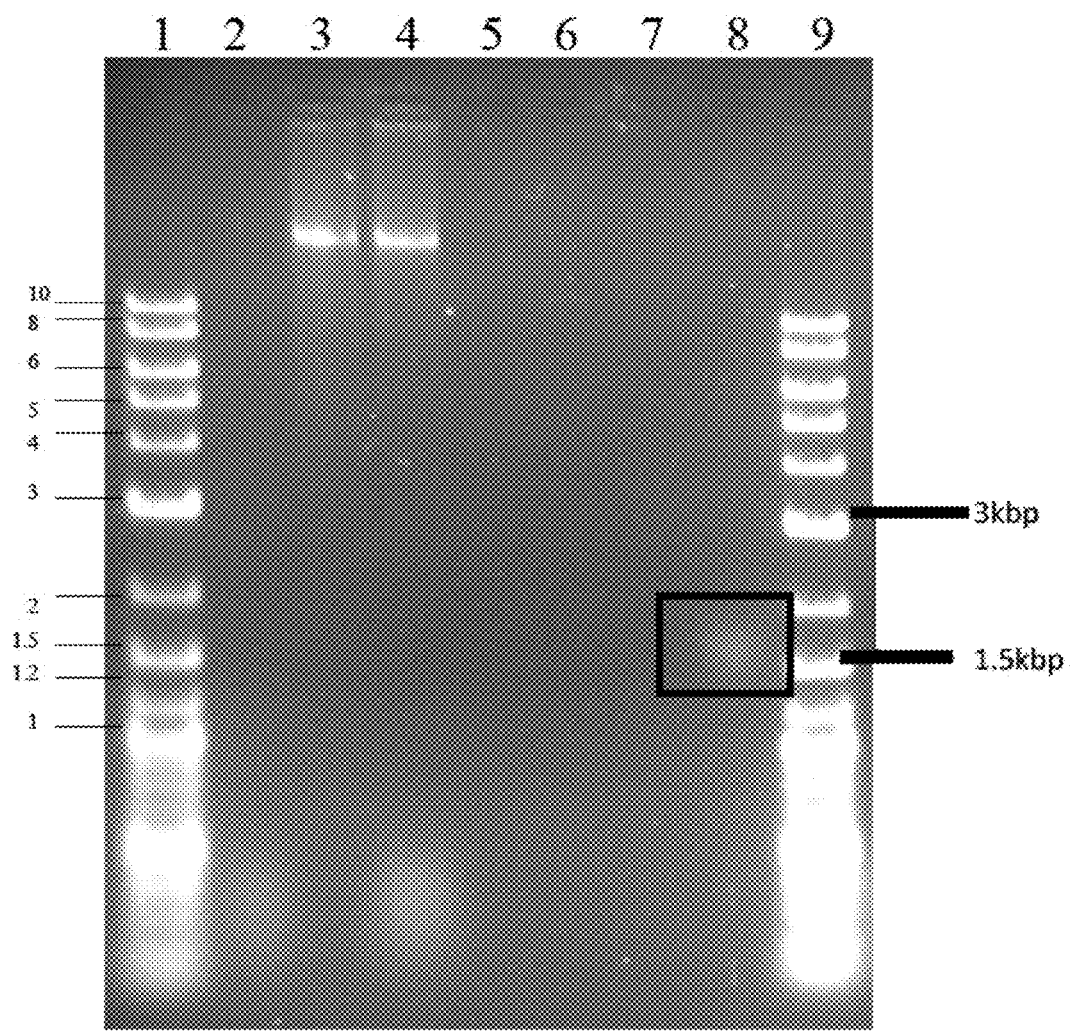
FIG. 8 shows an example of retrieving target DNA using a biotinylated 200 base oligonucleotide as the capture fragment. One nanomole of a biotinylated 200 base oligonucleotide was used to target the region upstream of the gltS gene from genomic DNA isolated from *E. coli* MG1655. Following the double strand break reaction, streptavidin-coated magnetic beads (Dynal M-280) were used to recover captured DNA. Fragments were freed from the magnetic beads by heating them to 65° C. in the presence of 95% formamide. Freed fragments are separated on 1% agarose gel and visualized with SYBR-Gold. Lanes 1 and 9 contain the TriDye-2 log ladder; sizes in kbp are indicated. Lane 2 is 1 nmol of the 200 base pair capture fragment. Lane 3 is 150 ng of *E. coli* MG1655 genomic DNA. Lane 4 combines the 200 base capture fragment and the *E. coli* genomic DNA. Lane 6 is the material released from the magnetic beads when they are treated with water. Lane 7 is the material released from the magnetic beads when they are treated with 95% formamide for five minutes at 65° C. Lane 5 is empty.
Figure 9:
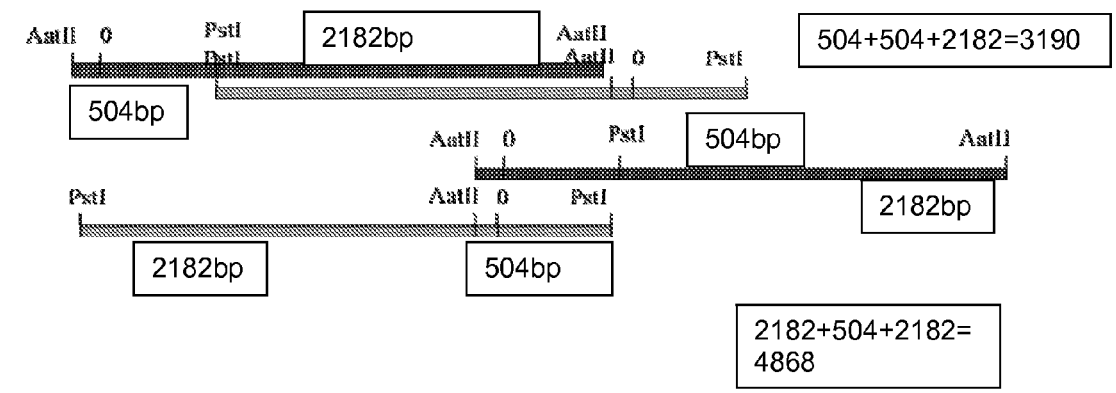
FIG. 9 is a diagram demonstrating the DNA products and their lengths of Example 1.

As illustrated in FIG. 8, a 200 base oligonucleotide initiates the double strand break reaction and allows us to retrieve a discrete set of fragments that are larger than 1500 base pairs (boxed in the figure). The protocol for retrieval and release works when 95% formamide is used to separate streptavidin and biotin. The same result was obtained using oligonucleotides of 150 and 100 bases in length, but the double-strand break reaction was not initiated with a 50 base oligonucleotide.

Example 3

DNA Double-Strand Break Repair in Forensic DNA Samples (Prophetic)

Short Tandem Repeat (STR) Typing

DNA genotyping based on the PCR amplification and electrophoretic analysis of STRs plays a prominent role in forensic science (Butler, J. M. 2006a; Butler, J. M. 2006b). A STR is a polymorphism found in mammalian DNA, a sequence of nucleotides (ranging between 2-10 base pairs) that is tandemly repeated at a locus. By examining several STR loci one can establish the unique genetic profile of an individual, linking biological evidence from a crime to the perpetrator or to other crimes by the same person.

Autosomal STRs

Tetranucleotide repeats are the mainstay of forensic DNA typing and criminal offender databasing (Butler, J. M. 2006a; Butler, J. M. 2006b). There are only 33 possible tetranucleotide motifs (Jin, L., et al. 1997), and the consensus motif sequences, mostly AGAT and GATA, are ubiquitous in the human genome. The number of repeat units at these loci varies from as few as four to as many as fifty. In 1997, the forensic community in the United States chose thirteen STR loci to form the essential core of its Combined DNA Index System (CODIS) casework and offender databases. These loci are: D3S1358, D5S818, D7S820, D8S1179, D13S317, D16S539, D18S51, D21S11, CSF1PO, FGA, Th01, TPOX, and VWA. There are enough different alleles at these STR loci in any major population or subpopulation to ensure that individuals will be heterozygous at most loci, enabling unambiguous identification (Butler, J. M. 2006a; Butler, J. M. 2006b).

Non-Autosomal DNA Sequences

Although the application of autosomal STRs for identification has been the principle focus of forensic scientists, situations arise in which it is useful to examine non-autosomal DNA sequences. Forensic Y chromosome STRs and mitochondrial DNA (mtDNA) analyses have become commonplace in laboratories working in crime casework all over the world.

Y chromosome STRs are repeat sequences similar to those described in Table 1. The male specificity of the human Y chromosome allows identification of paternally related individuals (The Y chromosome is passed from father to son), and is particularly useful in establishing paternity of male children and identifying the male component of male/female admixtures in forensic samples such as those obtained during a rape investigation.

The protocol for conducting Y chromosome STR analysis is identical to that used in analysis of autosomal STRs, except a different set of loci is amplified. Targeting fragments specific could be designed, as described in paragraphs [0043]-[0044], for Y chromosome STRs, and used to retrieve Y chromosome STRs as necessary.

Forensic scientists turn to mitochondrial DNA (mtDNA) when nuclear DNA based STR approaches fail, usually because of decomposition of the forensic sample. Mitochondria are present in enormous numbers in cells and because they exist in an exonuclease resistant circular form they are more stable, persisting long after the nuclear DNA has degraded. Mitochondrial DNA can be retrieved from the bones of individuals that have been dead for centuries and this technique was recently used to identify a novel human ancestor that existed 1,000,000 years ago (Krause, J., et al., 2010). Mitochondrial DNA is generally inherited maternally, making it easier to establish the identity of the individual trough the mother or siblings. The method is often used to identify skeletal remains and establish family relationships from buried ancestors (Holland, M. M., et al. 1993; Hagelberg, E., et al. 1991 and Ivanov, P. L., et al. 1996).

Analysis of mtDNA is currently accomplished by sequencing the DNA from hypervariable regions 1 and 2 (HV1/HV2) of the displacement loop (nucleotides 16024-16576) (Budowle, B., et al. 1999). The nucleotide polymorphisms found by sequencing identify the individual. As with the STRs, the hypervariable regions are flanked by conserved sequence that would allow their retrieval from complex mixture following double strand break repair, extending the use of the invention to all markers commonly used in forensic analysis. The protocol for conducting mtDNA HV1/HV2 analysis is identical to that used in analysis of autosomal STRs, except a different set of loci is amplified. Targeting fragments specific could be designed, as described in paragraphs [0043]-[0044], for HV1/HV2, and used to retrieve HV1/HV2 sequences as necessary.

DNA Degradation and STR Typing

Figure 4:
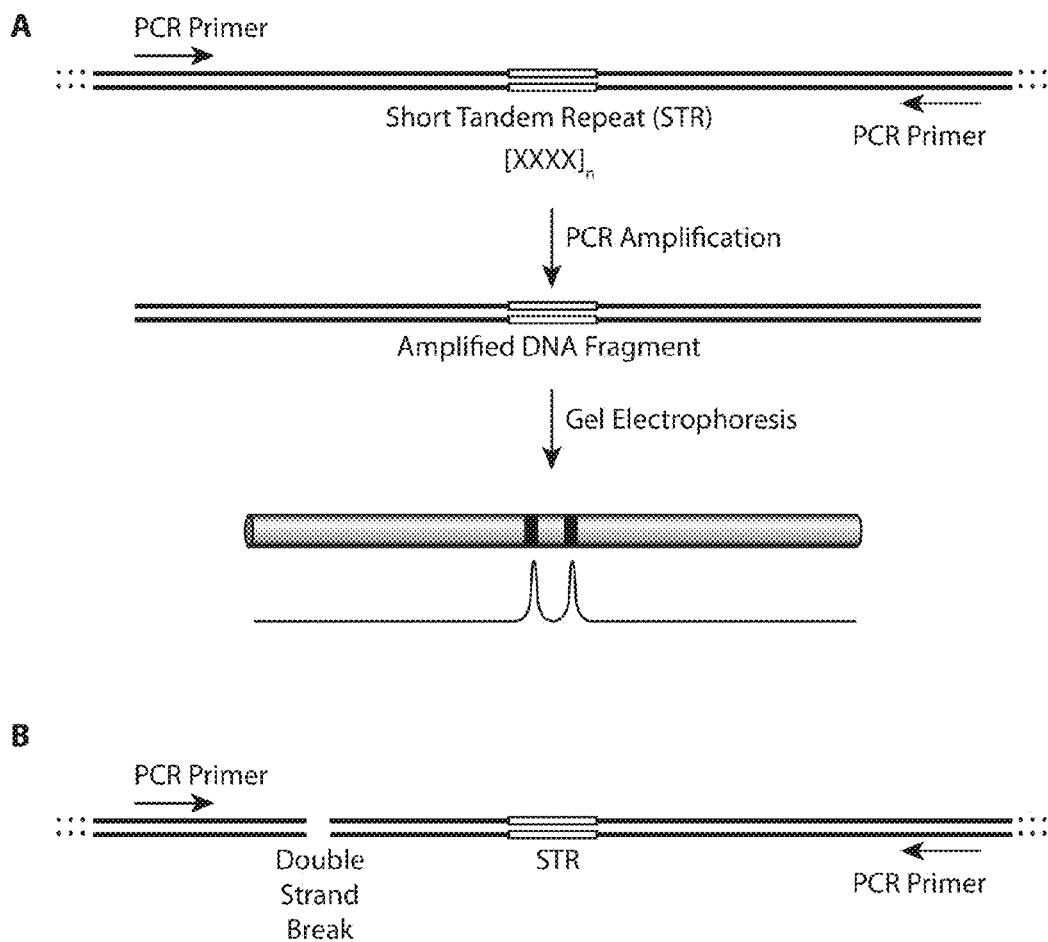
FIG. 4 A-B shows the use of short tandem repeat (STR) sequences in forensic DNA typing. (A) The STRs that are used consist of 4 nucleotide repeats, generally organized in tandem arrays of 5 to 40 copies. PCR primers are targeted to nonrepetitive DNA, found in every human, on either side of an STR. When the region between the primers is amplified, the fragment length will depend on the length of the repeat on a particular chromosome. Since each human has two copies of each STR, one inherited from his/her mother and the other from his/her father, most individuals have two different alleles of any given STR, and this generates two bands when the PCR products are subjected to gel electrophoresis. (B) A double-strand break occurring anywhere between the PCR primers will prevent amplification.

Under conditions where biological samples are well-preserved, genotyping using STRs is a robust technology that can be applied with confidence. However, forensic scientists are often confronted with biological evidence in which the DNA is present in a degraded form that interferes with PCR amplification, limiting the effectiveness of this technology (Hochmeister, M. N. 1998; Hoff-Olsen, P., et al. 2001; Pfeiffer, H., et al. 1999). In these samples the DNA is highly fragmented and contains a large number of modified nucleotides. STR analysis generates PCR fragments of between 100-500 base pairs; if the fragments of target DNA are on average smaller than this, effective PCR amplification will not be obtained. Although many other types of DNA damage can interfere with PCR amplification, double-strand breaks are the major impediment to successful DNA genotyping in degraded DNA samples. Any double-strand break in the region between the primers used to amplify the DNA at a particular locus will prevent amplification of that segment (FIG. 4).

One embodiment of the invention, comprises a kit of four components: a set of targeting DNA segments (described below) that encompass DNA sequences flanking each STR used for forensic DNA genotyping, RecA protein, SSB protein, and DNA polymerase. Preferable additions include a buffering solution that includes ATP (dATP may substitute in this first step), and the four deoxynucloside triphosphate substrates of DNA polymerases (dATP, dGTP, dCTP, and dTTP).

Each of the targeting DNA fragments will encompass approximately 150-400 bp to one side of an analyzed STR. Separate targeting fragments will encompass DNA on either side of a given STR. As there are 16 STRs used in a standard DNA genotyping kit, there will be 32 separate targeting DNA fragments in this embodiment of the invention. Each targeting fragment will be designed so the end of the sequence corresponds to a position 2-10 bp away from the end of the STR, preferably a position 4-8 bp away from the end of the STR. STR sequences themselves will not be part of any of the fragments. In addition, each targeting fragment is designed so that the 3' end that is proximal to the STR ends in a nucleotide that is not present in the STR. Each targeting fragment consists of two DNA strands, here designated an invasion strand and a complementary strand as defined in FIG. 5.

Figure 5:
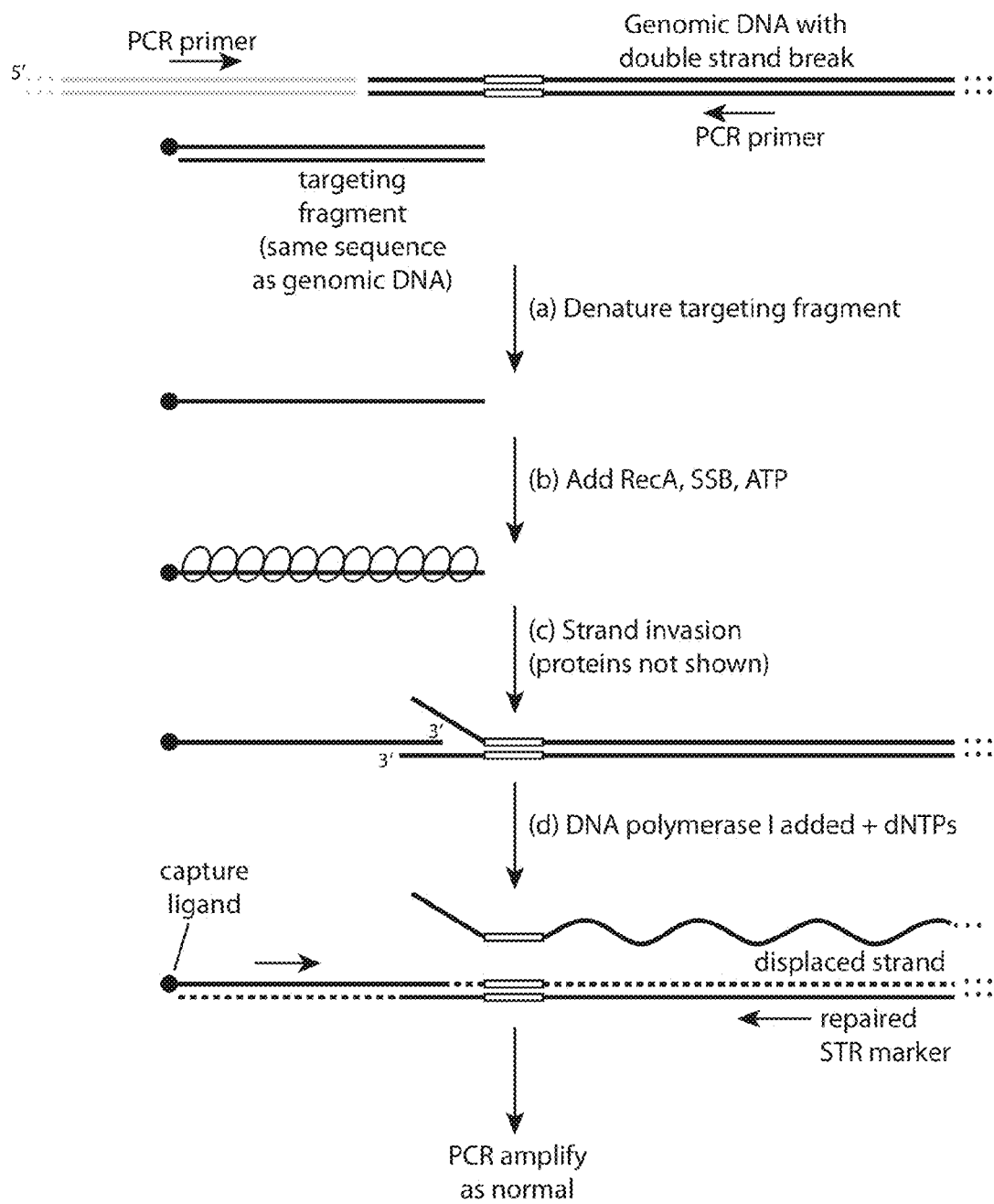
FIG. 5 shows one embodiment of the invention which applies the in vitro DNA double-strand break repair to forensic DNA typing. A double-strand break between the STR (shown as open bar) and the site targeted by the PCR primer will prevent the generation of a signal in forensic DNA typing. Such breaks can be repaired by double-strand break repair in vitro. The targeting fragment will be denatured, preferably by heat denaturation, by asymmetric PCR, or by nuclease/helicase treatment, to generate the single-strand that has a 3' end proximal to the STR. Alternatively, the single-stranded targeting DNA fragment can be directly synthesized. The ssDNA will be bound by RecA and SSB and used in a strand invasion reaction. The strand invasion involves DNA sequences flanking the STR, and does not affect the STR itself (double-strand breaks within the STR cannot be repaired without a potential alteration of repeat length). By targeting only adjacent DNA, double-strand breaks can be repaired without affecting STR length. The repaired segments will generate accurate forensic DNA typing signals in cases where none were possible prior to repair.

DNA double-strand break repair of forensic DNA, is illustrated in general in FIG. 5. The targeting fragments will be denatured by heat or the complementary strand will be removed by nucleolytic digestion followed by careful removal of the nuclease (FIG. 5A). Asymmetric PCR may also be used to generate single strand targeting fragments. Alternatively, the targeting fragments can simply be synthesized directly. RecA protein and SSB are both added to the single-stranded DNA, along with the various nucleoside triphosphates (FIG. 5B). The mixture will be added to a forensic DNA sample. If a double-strand break exists near an intact STR, strand invasion will occur (FIG. 5C). DNA polymerase, preferably DNA Pol I, is then added, extending the invading 3' end (FIG. 5D). The same DNA polymerase then extends the second strand of the STR-containing DNA, producing a duplex DNA fragment with a longer region of intact DNA on the repaired side of the STR (FIG. 5D). The additional length provides the contiguous DNA needed for successful amplification of the STR by PCR (FIG. 5E).

Example 4

Extraction of Specific New Segments of DNA from an Ancient Source (Prophetic)

Ancient DNA (aDNA) refers to DNA isolated from sources that have an archaeological or historical significance. Examples include, but are not limited to, mummified tissues, ancient skeletal remains, preserved materials found in museums, and archived medical specimens. These samples are complex mixtures like other environmental materials, but differ in that they contain modern and aDNA from bacterial and eukaryotic sources. Unlike modern DNA, aDNA will be degraded, existing as fragments of varying sizes further complicating analysis.

Figure 6:
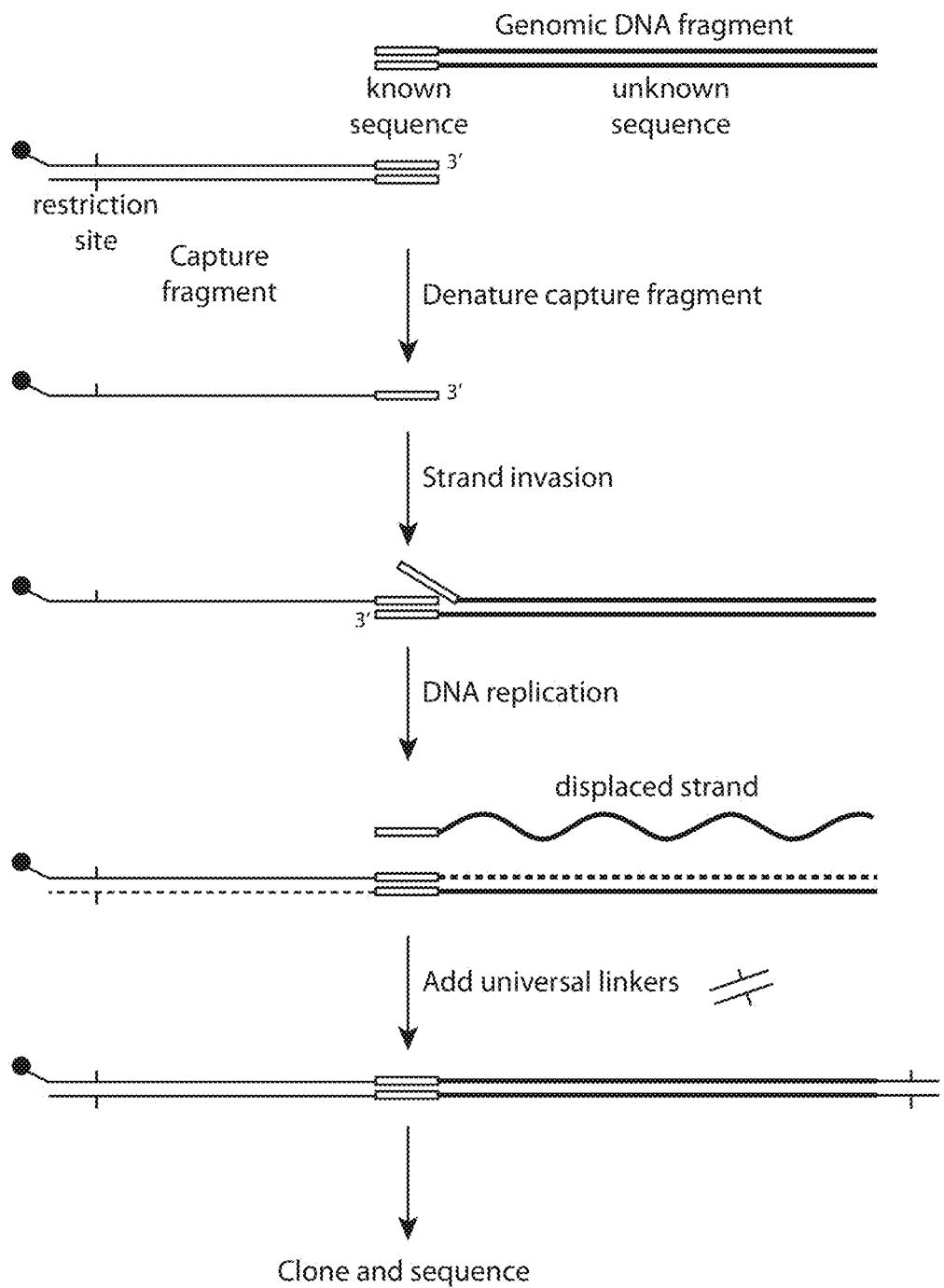
FIG. 6 shows a scheme for the capture of DNA segments of unknown sequence from complex mixtures of DNA fragments, using double-strand break repair in vitro. The capture fragment features a segment of known sequence DNA at one end. This fragment is used as a probe for strand invasion of segments that have sequence overlapping the known portion and subsequent extending beyond the known portion. The addition of a capture ligand (e.g., biotin) allows the facile retrieval of captured DNA segments. The further addition of universal linkers on the far end of the captured segment and proper design of the capture fragment so it includes a convenient restriction site allow for simplified cloning of the captured segments. All steps in this scheme are readily automated.

The procedure is illustrated in FIG. 6. First, a targeting probe sequence is generated that includes sequence information previously derived from the ancient tissue or bone sample. This known and cloned sequence information is amplified by PCR such that a targeting DNA strand is generated with a capture ligand at the 5' end. By "capture ligand", we mean small molecules added to the 5'-end of the DNA strand that allow for the retrieval of DNA. The DNA is denatured, and used to probe the sample. If there are any DNA segments present in the sample that have sequence information overlapping that in the targeting DNA strand, the RecA and SSB will promote strand invasion, followed by extension of the invading strand by DNA polymerase I. The DNA thus lengthened, and incorporating DNA of contiguous but unknown sequence, can be retrieved using the capture ligand (FIG. 6).

The major advantage of the procedure described above lies in its ability to separate the sequences of interest from everything else in the mixture and manipulate them in isolation. As long as authentic DNA sequence information can be derived from aDNA fragments of interest, targeting DNA can be generated and used to selectively capture adjacent sequences from the sample. The use of homologous DNA sequences ensures that DNA associated with contaminating biological material will not be incorporated into the new construct. The use of a capture ligand will facilitate purification from contaminating biological material and automation of the procedure.

Example 5

Use of DNA Double-Strand Break Repair to Fill in Sequencing Gaps in Genome Sequencing Projects (Prophetic)

Whole genome shotgun sequencing is a method that fractures a species genome into a myriad of random fragments that are then sequenced without regard to their order. As more and more sequence information becomes available these short "reads" are electronically assembled into larger contigs that eventually are assembled into the genome.

Closing a genome (filling in any gaps or sorting out areas of ambiguity that remain near the end of the sequencing project) is frequently the slow step in the assembly of a genome. Selective capture following homologous recombination provides a rapid method for closing a genome sequencing project. Using unambiguous DNA sequence found next to sites that need to be closed, targeting DNA fragments can be generated that will retrieve adjacent DNA. The specificity of homologous recombination and iterative application of the present method allows gaps to be filled from both ends.

As in FIG. 6, a targeting strand would be constructed based on known sequence information immediately adjacent to the sequence gap. Fragmented genomic DNA would then be subjected to strand invasion by the targeting strand, with the aid of RecA and SSB. Extension of the invading strand would then replicate across the DNA encompassing the sequence gap, permitting its cloning and simplifying further analysis.

Example 6

Use of DNA Double-Strand Break Repair in Metagenomics (Prophetic)

Metagenomics is a term originally used to describe the sequencing and analysis of genetic material obtained from environmental samples.

Selective capture following homologous recombination will benefit the study of metagenomics by allowing investigators to isolate and characterize specific DNA sequences within the complex mixtures of DNA obtained from environmental samples. If a segment of DNA is in hand from one species of interest in a broader interdependent community, double-strand break repair in vitro can be used to capture adjacent, overlapping segments of DNA from the same species. This technique permits an investigator to study bacterial communities, bypassing the need to isolate and cultivate individual species. In this embodiment, all DNA found in a sample is purified, and subjected to shotgun sequencing. Related sequences are then computationally assembled into larger contigs, reconstructing partial genomes of the species that made up that environmental community.

The procedure would be essentially the same as that shown in FIG. 6. First, a probe sequence is generated that includes sequence information previously derived from the species of interest. This known and cloned sequence information is again amplified by PCR such that a targeting DNA strand is generated with a capture ligand at the 5' end. The DNA is denatured, or rendered single-stranded by asymmetric PCR or nuclease/helicase action, and used to probe the sample using the double-strand break repair process of Example 1. If there are any DNA segments present in the broader sample that have sequence information overlapping that in the targeting DNA strand, the RecA and SSB will promote strand invasion, followed by extension of the invading strand by DNA polymerase I. The DNA thus lengthened, and incorporating DNA of contiguous but unknown sequence, can be retrieved using the capture ligand (FIG. 6).

Example 7

Automation (Prophetic)

All of the examples above are readily automated and can be applied to additional applications. Single stranded targeting fragments of 40 to 100 nucleotides, preferably 40 to 80 nucleotides, may be synthesized directly on a silicon chip (for example, using photolithography and other technologies developed by several companies). These can be used to probe DNA samples from any source, followed by DNA sequencing of the captured DNA fragments. Such an approach could be used to capture subsets of genomic sequences (e.g., all of the sequences adjacent to particular types of regulatory sequences or repeated sequences) for analysis.

REFERENCES

Bazemore, L. R., et al. (1997) RecA tests homology at both pairing and strand exchange. *Proc. Natl Acad. Sci. USA*, 94:11863-11868.

Blanco, L. and Salas, M. (1984) Characterization and purification of a phage phi29-encoded DNA polymerase required for the initiation of replication. *Proc. Natl Acad. Sci. USA*, 81:5325-5329.

Budowle, B., et al. (1999) Mitochondrial DNA regions HVI and HVII population data. *Forensic Sci. Int.* 103:23-35.

Butler, J. M., (2006a) Forensic DNA Typing, 2 ed. Academic Press, New York.

Butler, J. M., (2006b) Genetics and genomics of core short tandem repeat loci used in human identity testing. *J. Forensic Sci.* 51:253-265.

Cox, J. M., et al. (2008) Defective dissociation of a "slow" RecA mutant protein imparts an *Escherichia coli* growth defect. *J. Biol. Chem.* 283:24909-24921.

D'Abbadie, M., et al., (2007) Molecular breeding of polymerases for amplification of ancient DNA. *Nat. Biotechnol.* 25:939-943

Gruenig, M. C., et al. (2008) RecA-mediated SOS induction requires an extended filament conformation but no ATP hydrolysis. *Mol. Microbiol.* 69:1165-1179.

Hagelberg, E., et al. (1991) Identification of the skeletal remains of a murder victim by DNA analysis. *Nature* 352: 427-429.

Hänni, C., et al., (1995) Isopropanol precipitation removes PCR inhibitors from ancient bone extracts. *Nucleic Acids Res.* 23: 881-882.

Hochmeister, M. N., (1998) PCR analysis of DNA from fresh and decomposed bodies and skeletal remains in medicolegal death investigations. *Methods Mol. Biol.* 98:19-26.

Hofreiter, M., et al., (2004) Evidence for reproductive isolation between cave bear populations. *Curr. Biol.* 14:40-43.

Hoff-Olsen, P., et al., (2001) Microsatellite stability in human post-mortem tissues. *Forensic Sci. Int.* 119:273-278.

Holland, M. M., et al. (1993) Mitochondrial DNA sequence analysis of human skeletal remains: identification of remains from the Vietnam War. *J. Forensic Sci.* 38:542-553.

Ivanov, P. L., et al. (1996) Mitochondrial DNA sequence heteroplasmy in the Grand Duke of Russia Georgij Romanov establishes the authenticity of the remains of Tsar Nicholas II. *Nat. Genet.* 12:417-420.

Kalmar, T., et al., (2000) A simple and efficient method for PCR amplifiable DNA extraction from ancient bones. *Nucleic Acids Res.* 28, E67.

Krause, J., et al., (2010) The complete mitochondrial DNA genome of an unknown hominin from southern Siberia. *Nature* 464:894-897

Leonard, J. A., et al., (2000) Population genetics of ice age brown bears. *Proc. Natl. Acad. Sci. USA* 97:1651-1654.

Lohman, T. M., et al. (1986) Large-scale overproduction and rapid purification of the *Escherichia coli* ssb gene product. Expression of the ssb gene product under lambda PL control. *Biochemistry* 25:21-25

Jin, L., et al. (1997) Defining microsatellite alleles by genotyping global indigenous human populations and non-human primates. *J. Forensic Sci.* 42:496-499.

Pfeiffer, H., et al. (1999) Influence of soil storage and exposure period on DNA recovery from teeth. *Int. J. Legal Med.* 112:142-144.

Rao, B. J. and Radding, C. M. (1994) Formation of base triplets by non-Watson-Crick bonds mediates homologous recognition in RecA recombination filaments. *Proc. Natl Acad. Sci. USA,* 91:6161-6165.

Rondon, M. R., et al., (2000) Cloning the soil metagenome: a strategy for accessing the genetic and functional diversity of uncultured microorganisms. *Appl. Environ. Microbiol.* 66:2541-2547.

Tettelin, H., et al. (1999) Optimized multiplex PCR: efficiently closing a whole-genome shotgun sequencing project. *Genomics,* 62:500-507.

Shan, Q., et al. (1996) DNA strand exchange promoted by RecA K72R. *J. Biol. Chem.* 271:5712-5724

We claim:

1. A method of repairing a DNA double-strand break in vitro, comprising the steps of:
   (a) providing a duplex DNA molecule wherein the molecule has a double-strand break and wherein the molecule is not super-coiled;
   (b) providing a single-stranded DNA targeting fragment, wherein 3' end of the targeting fragment is homologous to at least 15 nucleotides of known sequence in the DNA molecule of step (a) and wherein sequence of the double-stand break is within the targeting fragment;
   (c) adding RecA protein or RecA protein homologue to the targeting fragment;
   (d) adding single-stranded DNA binding protein (SSB) or SSB homologue;
   (e) adding the DNA molecule of step (a) to the mixture resulting from step (d) and incubating until a strand invasion of the targeting fragment into the DNA molecule of step (a) has occurred; and
   (f) adding DNA polymerase and dNTPs, wherein the proteins of steps (c) and (d) and the polymerase of step (f) are the only strand-repair proteins added to the system, and incubating the resulting mixture until the invading strand has extended, wherein the strand comprises sequences from the targeting fragment and the DNA molecule of step (a).

2. The method of claim 1, wherein the resulting extended DNA of step (f) is amplified and analyzed.

3. The method of claim 1, wherein at least one of the group comprising the RecA protein and/or RecA homologue, SSB and/or SSB homologue, and DNA polymerase is from bacterial sources.

4. The method of claim 3, wherein the bacterial source is *Escherichia coli*.

5. The method of claim 1, wherein the DNA polymerase is selected from the group consisting of DNA polymerase I, DNA polymerase V, phi29 DNA polymerase and engineered translesion synthesis DNA polymerases.

6. The method of claim 1, wherein step (b) comprises the steps of providing a targeting fragment in a double-stranded form and converting the double-stranded targeting fragment to single-stranded DNA.

7. The method of claim 1, wherein step (c) is in the presence of a suitable buffer for RecA protein or RecA homologue, containing an ATP regenerating system.

* * * * *

UNITED STATES PATENT AND TRADEMARK OFFICE
CERTIFICATE OF CORRECTION

PATENT NO. : 8,586,362 B2
APPLICATION NO. : 12/796258
DATED : November 19, 2013
INVENTOR(S) : Michael M. Cox et al.

It is certified that error appears in the above-identified patent and that said Letters Patent is hereby corrected as shown below:

In the Specification

Column 2, Line 57 -- "150-400 by homology" should be --150-400 bp homology--

Column 11, Line 23 - in Table 1 Column Locus "TPDX" should be --TPOX--

Column 11, Line 43 - in Table 1 footnote "Number of differenct" should be --Number of different--

Signed and Sealed this
Twenty-fourth Day of June, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,586,362 B2  Page 1 of 1
APPLICATION NO. : 12/796258
DATED : November 19, 2013
INVENTOR(S) : Michael M. Cox et al.

It is certified that error appears in the above-identified patent and that said Letters Patent is hereby corrected as shown below:

Title Page, item [73]

In addition to Assignee: Wisconsin Alumni Research Foundation add:

-- Assignee: Board of Supervisors of Louisiana State University and Agricultural and Mechanical College 3810 W. Lakeshore Drive, Baton Rouge, Louisiana 70808 US --

Signed and Sealed this
Eighteenth Day of November, 2014

Michelle K. Lee
*Deputy Director of the United States Patent and Trademark Office*

```
                          SEQUENCE LISTING

<160> NUMBER OF SEQ ID NOS: 6

<210> SEQ ID NO 1
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 1
agtgacaaat tgagacctt                                                 19

<210> SEQ ID NO 2
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 2
aaggtctcaa tttgtcact                                                 19

<210> SEQ ID NO 3
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 3
tagcaactgt tataagaa                                                  18

<210> SEQ ID NO 4
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 4
ttcttataac agttgcta                                                  18

<210> SEQ ID NO 5
<211> LENGTH: 74
<212> TYPE: DNA
<213> ORGANISM: Homo sapiens

<400> SEQUENCE: 5
agtgacaaat tgagaccttg tctcagaaag aaagaaagaa agaaagaaag aaatagtagc    60
aactgttata agaa                                                     74
```

```
<210> SEQ ID NO 6
<211> LENGTH: 74
<212> TYPE: DNA
<213> ORGANISM: Homo sapiens

<400> SEQUENCE: 6
ttcttataac agttgctact atttctttct tctttctttt ctttctttct gagacaaggt      60
ctcaatttgt cact                                                       74
```